(12) United States Patent
Bresch et al.

(10) Patent No.: US 10,159,443 B2
(45) Date of Patent: Dec. 25, 2018

(54) APPARATUS AND METHOD FOR DETERMINING VITAL SIGNS FROM A SUBJECT

(71) Applicant: KONINKLIJKE PHILIPS N.V., Eindhoven (NL)

(72) Inventors: Erik Bresch, Eindhoven (NL); Jens Muehlsteff, Aachen (DE); Mukul Julius Rocque, Eindhoven (NL); Marek Janusz Bartula, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1329 days.

(21) Appl. No.: 14/200,481

(22) Filed: Mar. 7, 2014

(65) Prior Publication Data

US 2014/0276098 A1   Sep. 18, 2014

Related U.S. Application Data

(60) Provisional application No. 61/778,619, filed on Mar. 13, 2013.

(30) Foreign Application Priority Data

Mar. 13, 2013   (EP) .................................. 13158888

(51) Int. Cl.
*A61B 5/00* (2006.01)
*A61B 5/0205* (2006.01)
*A61B 5/024* (2006.01)
*A61B 5/08* (2006.01)
*A61B 5/103* (2006.01)

(52) U.S. Cl.
CPC .......... *A61B 5/7235* (2013.01); *A61B 5/0077* (2013.01); *A61B 5/0205* (2013.01);
(Continued)

(58) Field of Classification Search
CPC .............. A61B 5/0077; A61B 5/02416; A61B 5/07235
See application file for complete search history.

(56) References Cited

U.S. PATENT DOCUMENTS 5,704,367 A   1/1998   Ishikawa et al.
6,110,123 A   8/2000   Ishihara et al.
(Continued)

FOREIGN PATENT DOCUMENTS

EP   2438849 A1   4/2012
JP   2014171574   9/2014
(Continued)

OTHER PUBLICATIONS

Addison, P. S., et al.; Developing an algorithm for pulse oximetry derived respiratory rate (RRoxi): a healthy volunteer study; 2012; J. Clin. Monit. Comput.; 26:45-51.
(Continued)

*Primary Examiner* — Alyssa M Alter

(57) ABSTRACT

An apparatus and a method for determining vital sign information from a subject are disclosed. The proposed apparatus comprises a detection unit for detecting radiation received from the subject in a field of view, a first determining unit for determining a first time dependent signal from the radiation received from the subject, an evaluation unit for deriving at least one parameter from the first time dependent signal, a selection unit for selecting an area in the field of view on the basis of the detected radiation and the at least one parameter, a second determining unit for determining a second time dependent signal from the radiation received from the selected area, and an analysis unit for analyzing the second time dependent signal and for determining the vital sign information on the basis of the analysis of the second time dependent signal.

17 Claims, 8 Drawing Sheets

(52) U.S. Cl.
CPC ........ *A61B 5/02416* (2013.01); *A61B 5/0816* (2013.01); *A61B 5/1032* (2013.01); *A61B 5/721* (2013.01)

(56) References Cited

U.S. PATENT DOCUMENTS

| | | |
|---|---|---|
| 2009/0141124 A1 | 6/2009 | Liu et al. |
| 2011/0311119 A1 | 12/2011 | Jeanne et al. |
| 2011/0311143 A1 | 12/2011 | Cennini et al. |
| 2012/0195486 A1* | 8/2012 | Kirenko ............ A61B 5/02416 382/131 |

FOREIGN PATENT DOCUMENTS

| | | |
|---|---|---|
| WO | 2011135440 A1 | 11/2011 |
| WO | 2012140531 A1 | 10/2012 |

OTHER PUBLICATIONS

Orini, M., et al.; Estimation of Spontaneous Respiratory Rate from Photoplethysmography by Cross Time-Frequency Analysis; 2011; Computing in Cardiology; 38:661-664.

Nakai Hiroaki et al., "Respiration monitoring system by moving image processing", electronic information The journal of the Institute of Electronics, Information and Communication Engineers D, vol. J 83-D 2, N 0. 1, Jan. 25, 2000, pp. 280-288—English abstract only.

* cited by examiner

APPARATUS AND METHOD FOR DETERMINING VITAL SIGNS FROM A SUBJECT

CROSS REFERENCE TO RELATED APPLICATIONS

This application claims the benefit of U.S. provisional application Ser. No. 61/778,619 filed Mar. 13, 2013, and European provisional application serial no. 13158888.1 filed Mar. 13, 2013, both of which are incorporated herein by reference.

FIELD OF THE INVENTION

The present invention relates to an apparatus and method for determining vital sign information from a subject. In particular, the present invention relates to measurement approaches which can be used for remotely determining vital signs of an observed subject. In this context, optical measurements may refer to photo-plethysmography and to image pattern detection.

BACKGROUND OF THE INVENTION

Vital signs or a person, for example the heart rate, the respiration rate or the blood oxygen saturation, serve as indicators of the current state of a person and as powerful predictors of serious medical events. For this reason, vital signs are extensively monitored in impatient or outpatient care settings, at home or in further health, leisure and fitness settings.

One way of measuring vital signs is plethysmography. Plethysmography generally refers to the measurement of volume changes of an organ or a body part and in particular to the detection of volume changes due to a cardio-vascular pulse wave travelling through the body of a subject with every heartbeat. Plethysmography signals can be determined from a patient's skin by means of a remote photo-plethysmography measurement. Further, it is possible to derive a respiration signal from the photo-plethysmography signal received from the patient's skin color changes as described in WO 2011/135440 A1.

Further, camera-based remote monitoring methods for detecting vital signs of a patient, e.g. the respiration rate by means of motion pattern detection are known from WO 2012/140531 A1.

Since the camera-based photo-plethysmography is based upon skin detection of the patient to be measured and since the skin is not always visible in a field of view due to movement of the patient, the measurement of the respiration rate on the basis of the photo-plethysmography signal is not always reliable.

Further, since the area to be measured, e.g. the chest of the patient can be located freely in the field of view of the camera, it is difficult to determine the relevant portion from which the vital signs should be derived and the region of interest has to be selected in advance, wherein a movement of the subject may lead to faulty measurements.

The traditional identification of the region of interest in general is based on detection of human beings, e.g. a face or a chest or by using background segmentation. In order to identify a human being for measuring vital signs such as a pulse or respiration rate from a region of interest, US 2009/0141124 A1 suggest to detect a contour in an infrared video segment to select the region of interest representing a portion of a subject to be measured.

The disadvantage of the known methods for detecting a region of interest for a camera-based remote vital sign measurement is that an occlusion of a predefined region of interest or a movement of the subject within the field of view may lead to the measurement of disturbance signals and to faulty measurements in general.

SUMMARY OF THE INVENTION

It is an object of the present invention to provide an improved apparatus and an improved method for determining vital sign information of a subject which is more robust against disturbing signals in the field of view.

According to one aspect of the present invention, an apparatus for determining vital sign information from a subject is provided, comprising:

a detection unit that detects radiation received from the subject in a field of view, a first determining unit that determines a first time dependent signal from the radiation received from the subject, an evaluation unit that derives at least one parameter from the first time dependent signal, a selection unit that selects an area in the field of view on the basis of the detected radiation and the at least one parameter, a second determining unit that determines a second time dependent signal from the radiation received from the selected area, and an analysis unit that analyses the second time dependent signal and determines the vital sign information on the basis of the analysis of the second time dependent signal.

According to another aspect of the present invention, a method for determining vital sign information from the subject is provided, comprising the steps of:

detecting radiation received from the subject in a field of view, determining a first time dependent signal from the radiation received from the subject, deriving at least one parameter from the first time dependent signal, selecting an area in the field of view on the basis of the detected radiation and the at least one parameter, determining a second time dependent signal from the radiation received from the selected area, analyzing the second time dependent signal and determining the vital sign information from the analyzed second time dependent signal.

Preferred embodiments of the present invention are defined in the dependent claims. It shall be understood that the claimed method has similar or identical preferred embodiments as the claimed device and as defined in the dependent claims.

The present invention is based on the idea to derive at least one parameter from a detected signal received from the subject to be measured and to select the region of interest on the basis of the remote measurement and the derived parameter. The vital sign information is determined on the basis of a second time dependent signal which is received from the selected region of interest. Hence, the region of interest selection is based upon a first signal derived from the field of view and the measurement of the vital sign information is based upon a second parameter which is determined from the selected region of interest. Therefore, the region of interest can be determined on a coarse estimation of the vital sign information within the field of view and after the region of interest is identified in the field of view, the vital sign information can be determined precisely on the basis of the second parameter.

Due to the coarse determination of the vital sign information and the selection of the region of interest on the basis of the coarse vital sign information, the measurement of the vital sign information is more reliable and more robust against disturbing signals in the field of view since the selection of the region of interest is adapted individually to the signal parameter to be measured.

In a preferred embodiment, the evaluation unit comprises a frequency determining device that determines a frequency from the first time dependent signal as the at least one parameter. This is a simple possibility to determine a relevant parameter of the vital sign information in order to determine the region of interest with high precision and low technical effort.

In a preferred embodiment, the evaluation unit comprises a demodulation unit that determines a frequency from the first time dependent signal as the at least one parameter. This is a reliable possibility to determine the relevant vital sign information from the measured time dependent signal, since usually different signals are superimposed in the received radiation so that the demodulation of the first time dependent signal provides a coarse estimation of the vital sign information.

According to a preferred embodiment, the demodulation unit is a frequency demodulation unit that demodulates the first time dependent signal as a frequency modulated signal. This one possibility to derive the at least one parameter from the first time dependent signal if the time dependent signal is frequency modulated.

It is further preferred that the demodulation unit is an amplitude demodulation unit that demodulates the first time dependent signal as an amplitude modulated signal. This is a simple possibility to demodulate the first time dependent signal with low technical effort.

In a preferred embodiment, the evaluation unit comprises a filter device that filters the first time dependent signal and determines the at least one parameter. This is a simple solution to derive the at least one parameter from the first time dependent signal with low technical effort.

In a preferred embodiment, the detection unit comprises an imaging device that determines image data from the field of view. This is a preferred solution to provide a remote measurement of different physical parameter of the subject so that a flexible use of the apparatus can be provided.

In a preferred embodiment, the first time dependent signal is based upon a wavelength variation of the radiation received from the subject. This is a possibility to determine vital sign information from color changes of the subject e.g. a plethysmography signal.

According to a preferred embodiment, the selection unit is adapted to determine a plurality of alternating signals from different areas of the field of view and wherein the selection unit is adapted to select the area for determining the second time dependent signal on the basis of the alternating signals and on the basis of the at least one parameter. Since the selection unit determines the alternating signals from different areas of the field of view, the region of interest can be precisely selected in the whole field of view on the basis of the vital sign information to be measured. Hence, the selection of the region of interest is precise and the measurement is robust against disturbing signals.

It is preferred if the alternating signals determined from the different areas of the field of view correspond to movement pattern in the field of view and are determined on the basis of pattern detection. This is a practical and precise solution to determine the respiration rate of the subject from remote measurements.

It is further preferred if the at least one parameter is a bandwidth for filtering the alternating signals. This is a possibility to improve the robustness of the vital sign information detection since the bandwidth for filtering the vital sign information is adapted to the vital signal to be measured and removes disturbing signals usually having a different frequency.

In a further preferred embodiment, the first time dependent signal is received from a skin of the subject. This is a practical solution in order to detect a coarse vital sign information from the subject with low technical effort to select the region of interest for precise measurements.

In a further preferred embodiment, the detection unit comprises a first camera that determines the first time dependent signal and a second camera that determines the second time dependent signal. This increases the robustness and the reliability since the different cameras can be adapted to the respective measurements and can be handled independently.

In a further preferred embodiment, the first time dependent signal is a plethysmography signal. This is a simple solution to detect a coarse vital sign information from the subject with low technical effort in order to select the region of interest for a precise measurement of the vital sign information.

As mentioned above, the present invention provides an apparatus and a method for determining vital sign information from a subject which is less sensitive for disturbing signals since the region of interest for the remote measurements is selected on the basis of a signal received from the subject which is different from the signal for determining the vital sign information. In other words, a first time dependent signal is determined from the subject to be measured and used for determining the region of interest and for selecting the area in the field of view to measure the second time dependent signal on the basis of which the vital sign information is determined. Hence, since the selection of the region of interest is adapted to the signal parameter to be measured, the measurement is less sensitive for disturbing signals and the region of interest can be determined with high precision.

In still another aspect of the present invention a method for determining vital sign information from a subject is presented, comprising the steps of:

determining a first time dependent signal from image data determined from the subject in a field of view, deriving at least one parameter from the first time dependent signal, selecting an area in the field of view on the basis of the image data and the at least one parameter, determining a second time dependent signal from the selected area, analyzing the second time dependent signal and determining the vital sign information from the analyzed second time dependent signal.

According to still another aspect of the invention, a computer readable non-transitory medium is presented having instructions stored thereon which, when carried out on a computer, cause the computer to perform the steps of the method according to one aspect of the present invention.

In still another aspect of the present invention an apparatus for determining vital sign information from a subject is presented, comprising:

an image detection unit that detects image data received from the subject in a field of view, a first determining unit that determines a plethysmography signal from the image data received from the subject, an evaluation unit that derives a frequency spectrum from the plethysmography signal, a selection unit that selects an area in the field of view on the basis of the frequency spectrum, a second determining unit that determines a time dependent signal from the image data received from the selected area, and an analysis unit that analyses the time dependent signal and determines the vital sign information on the basis of the analysis of the second time dependent signal.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Figure 1:
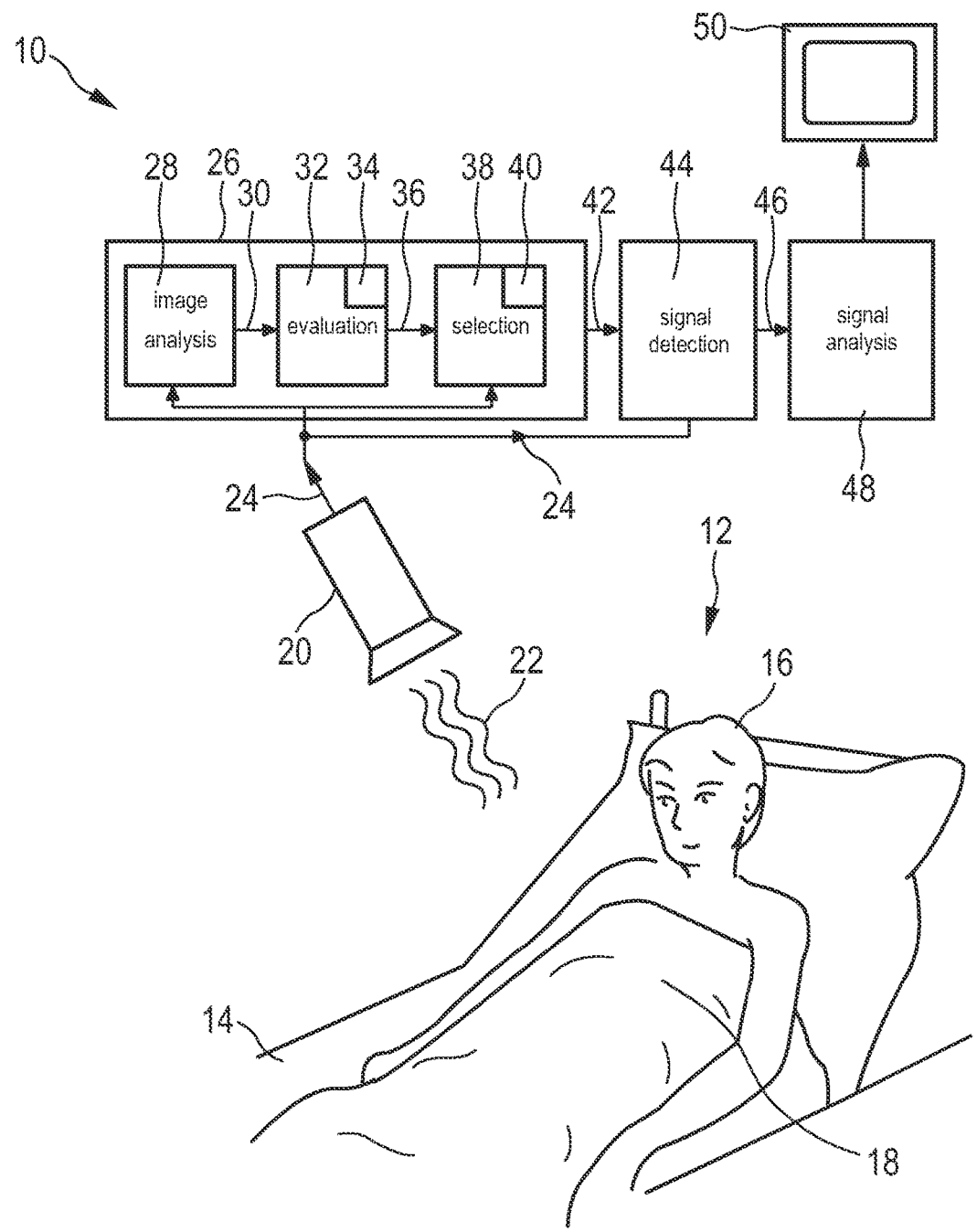
FIG. 1 shows a schematic illustration of a general layout of an apparatus for determining vital sign information from a subject.

FIG. 1 shows a schematic drawing of an apparatus generally denoted by 10 for determining vital sign information from a subject 12. The subject 12, i.e. a patient staying in bed, is resting on a support 14. The subject's head 16 is usually an indicative portion for a plethysmography signal in order to determine a heart rate or a blood pressure as vital sign information of the subject 12, wherein the chest 18 or the belly 18 is usually an indicative portion for the respiration of the subject 12, wherein a motion of the chest 18 is detected in order to measure the respiration rate of the subject 12. The general problem of the common situation shown in FIG. 1 is that the chest 18 as indicative portion for the respiration rate of the subject 12 has to be determined as region of interest in a field of view in order to perform a remote measurement of the vital sign information.

The apparatus 10 is provided to remotely measure a vital sign information from the subject 12 to determine a region of interest and to determine the vital sign information detected from the region of interest.

The apparatus 10 comprises an image detection device 20, e.g. a camera which can be used for recording image data 24 such as image frames or an image stream of the subject 12. The image data 24 can be derived from electromagnetic radiation 22 emitted or reflected by the subject 12. For extracting the image information from the image data 24, the image data 24 is provided to an image processing unit 26.

The image detection device 20 is adapted to capture images of a spectral range of the electromagnetic radiation 22. The image detection device 20 may provide continuous image data or a discrete sequence of image frames captured from a field of view including the subject 12 to be measured.

The image processing unit 26 is adapted to evaluate the image data 24 in general and to divide the captured images in sections or areas of the field of view and to evaluate the image section separately in order to determine a region of interest. The image processing unit 26 comprises a determining unit 28 which evaluates the image data 24 and detects the head 16 or the face of the subject 12 or another skin portion of the subject 12 in order to derive a first time dependent signal from the radiation 22 received from the subject 12. This first time dependent signal is determined from color changes of the skin of the subject 12, which is usually a plethysmography signal and comprises vital sign information of the subject 12 including e.g. the heart rate and the respiration rate of the subject 12.

The image processing unit 26 further comprises an evaluation unit 32 connected to the determining unit 28 in order to evaluate the first time dependent signal 30 received from the determining unit 28.

Since the first time dependent signal 30 is a plethysmography signal and comprises vital sign information such as heart rate and respiration rate, modulated or superimposed with another signal, the evaluation unit 32 comprises a frequency analysis unit 34 to separate the different vital sign information from the first time dependent signal 30. The frequency analysis unit 34 may be a filter device for filtering a predefined frequency range from the first time dependent signal 30 or a demodulation unit, which demodulates the first time dependent signal 30 as an amplitude modulation signal or a frequency modulation signal. The evaluation unit 32 extracts by means of the frequency analysis unit 34 a course respiration rate from the first time dependent signal 30 in order to estimate in which frequency range the respiration rate to be measured is to be expected. The extracted course respiration rate 36 is provided to a selection unit 38 connected to the evaluation unit 32.

The selection unit 38 receives the image data 24 and evaluates the image data 24 by means of a pattern detection unit 40. The selection unit 38 is adapted to divide the captured images in sections or areas of the field of view and to evaluate the image sections separately in order to determine the region of interest. The selection unit 38 divides the captured images into the sections of areas and detects motion vectors from the different sections corresponding to the motion of objects in the field of view including the motion of the subject 12 and, in particular, the motion of the chest 18 as an indicative portion for the respiration. The motion vectors are determined by a pattern detection unit 40 by means of pattern detection in the different image sections or by means of edge detection in the image sections. A method for edge or pattern detection and for deriving the motion vectors from the captured image frames is, for example, disclosed by WO 2012/140531 A1.

The pattern detection unit 40 determines alternating signals from the motion vectors of each of the sections. The selection unit 38 filters the alternating signals of each of the sections by means of a frequency filter or a filter bandwidth corresponding to the course respiration rate 36 received from the evaluation unit 32. By means of this filtering, the selection unit 38 selects the section of the field of view which comprises movement pattern corresponding to the course respiration rate 36 in order to determine automatically the region of interest for remote measurement of the respiration rate of the subject 12.

The selection unit 38 provides as an output signal 42 the information regarding the selected image sections or the information regarding the selected region of interest.

The image processing unit 26 is connected to a second determining unit 44, which receives the output signal 42 from the selection unit 38 including the information regarding the selected image section or the selected region of interest. The second determining unit further receives the image data 24 from the image detection device 20 in order to determining the vital sign information from the subject 12. The second determining unit 44 is adapted to evaluate the image data 24 and to determine a second time dependent signal from the selected area or the region of interest received from the selection unit 38. The second determining unit detects motion vectors in the selected section or the region of interest corresponding to the motion of the subject 12 which is usually the chest 18 of the subject 12 as the indicative portion of the respiration. From the motion vector, the second determining unit 44 determines an alternating signal including the vital sign information and forwards the alternating signal as an output signal 46 to an analysis unit 48.

The analysis unit 48 receives the alternating signal 46 and determines the vital sign information on the basis of the alternating signal, in particular the respiration rate of the subject 12 and forwards the vital sign information to a display unit 50 for displaying the vital sign information of the subject 12.

Hence, the apparatus 10 determines the region of interest on the basis of the plethysmography signal 30 determined from the skin of the subject 12 and determines the vital sign information, and particular the respiration rate of the subject 12 on the basis of pattern detection in the region of interest determined on the basis of the plethysmography signal 30.

The apparatus 10 may be provided without the camera 20 and may be adapted to receive the image data 26 from an external camera via an interface.

Figure 2:
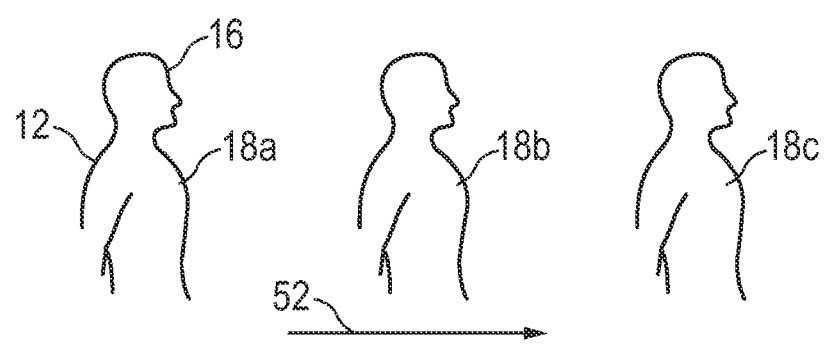
FIG. 2 shows a schematic illustration of a subject's motion indicative of an exemplary vital sign information.

FIG. 2 shows a schematic illustration of the subject 12 in order to describe the remote measurement of the respiration of the subject 12. The subject 12 undergoes a characteristic motion of an indicative portion 18 (the chest 18) due to the respiration. When breathing, expansion and contraction of the lung's courses slight motion of characteristic portions of liven beings, e.g. lifting and lowering of the chest 18. Also, abdominal breathing can course characteristic motion of respective parts of the subject's body 12. At least partially periodic motion patterns included by physiological processes can occur in many living beings, particularly in human beings or animals.

Over time, as indicated by an arrow 52, the indicative portion 18 is moved between a contracted position, indicated by reference numerals 18a, 18c, and an extracted portion, indicated by 18b. Essentially, based on this motion pattern, for instance the respiration rate or respiration rate variability can be assessed by means of pattern or edge detection in a captured image sequence. While the indicative portion 18 is pulsating over time, the head 16 as a non-indicative portion 16 remains substantially motionless.

Certainly, also the head 16 undergoes diverse motion over time. However, these motions do not correspond to the periodic pulsation of the chest 18 and can be distinguished by means of a frequency analysis.

Figure 3:
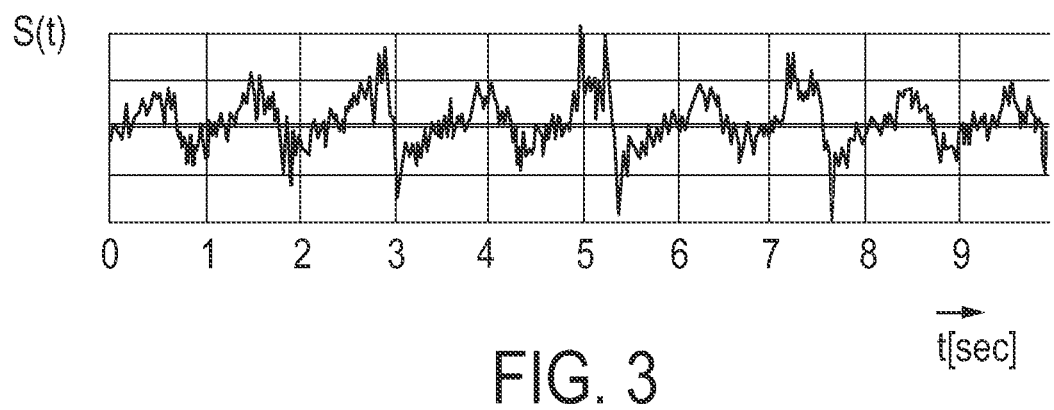
FIG. 3 shows a timing diagram of an alternating signal extractor from movement pattern of the subject to determine vital sign information.

FIG. 3 shows a timing diagram of an alternating signal derived from the movement pattern and/or from motion vectors of the different image sections which can be for example determined on the basis of a frame or an edge detection in the respective image section. The alternating signal is generally denoted by S(t). The alternating signal S in this particular case corresponds to the movement of the chest 18 of the subject 12 derived from an image section corresponding to the image data received from the respective indicative portion 18. The alternating signal S shows a characteristic variation corresponding to the movement of the chest 18, i.e. the breathing rate of the subject 12. The alternating signal S also shows a high-frequency noise superimposed to the breathing rate.

The alternating signals S are derived from each of the image sections of the field of view wherein a plurality of image sections comprise vital sign information such as a breathing rate and many image sections may comprise disturbing signals which are not related to vital sign information of the subject 12 or other alternating signals which comprise mostly high-frequency noise. In order to identify those image sections as the region of interest from which vital sign information can be derived, the selection unit 38 comprises a frequency analysis device to perform a frequency analysis of the alternating signals S.

The selection unit 38 selects a predefined filter bandwidth or determines an individual bandwidth on the basis of the course respiration rate 36 and filters the alternating signals S accordingly. The image sections which provide a vital sign information such as the respiration rate of the subject 12 can be determined as those image sections which provide an alternating signal after the filtering process.

In a certain embodiment those image sections are selected by the selection unit 38 which have a spectral energy of the alternating signals S in the selected frequency range larger than a predefined threshold value or larger than a certain portion compared to the spectral energy of the whole alternating signal. E.g. those image sections are selected as region of interest having 50% of the entire spectral energy of the alternating signals within the defined or determined spectral range.

Figure 4:
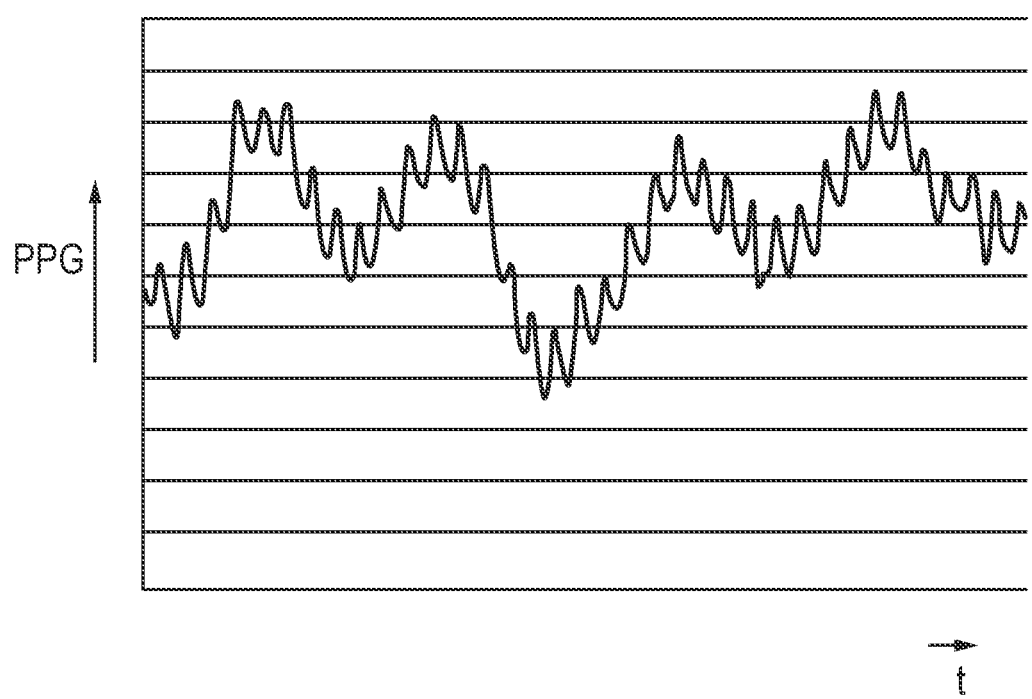
FIG. 4 shows a plethysmography signal extracted from a remote measurement of a subject's skin including different vital sign information.

FIG. 4 shows a photo-plethysmography signal (PPG), which corresponds to color changes of the skin of the subject 12 and comprises the information about the heartbeat of the subject 12 and the respiration rate of the subject 12. The photo-plethysmography signal (PPG) shown in FIG. 4 comprises a high frequency signal portion corresponding to the heart rate of the subject 12 and a slow oscillating signal portion corresponding to the respiration of the subject 12. Since the photo-plethysmography signal (PPG) is based on color changes over time and the respiration detection is based on the spatial movement of the chest of the subject 12, the plethysmography signal (PPG) extracted from the skin, e.g. the face, can be considered as separate channel information carrying information on the respiration of the subject 12.

Hence, not only the heart rate of the subject 12 can be derived from the photo-plethysmography signal (PPG) but also the respiration rate as a second oscillation or alternating signal component of the photo-plethysmography signal (PPG). The heart rate and the respiration rate of the subject 12 can be superimposed in the photo-plethysmography signal (PPG) in different ways as described in the following.

Figure 5:
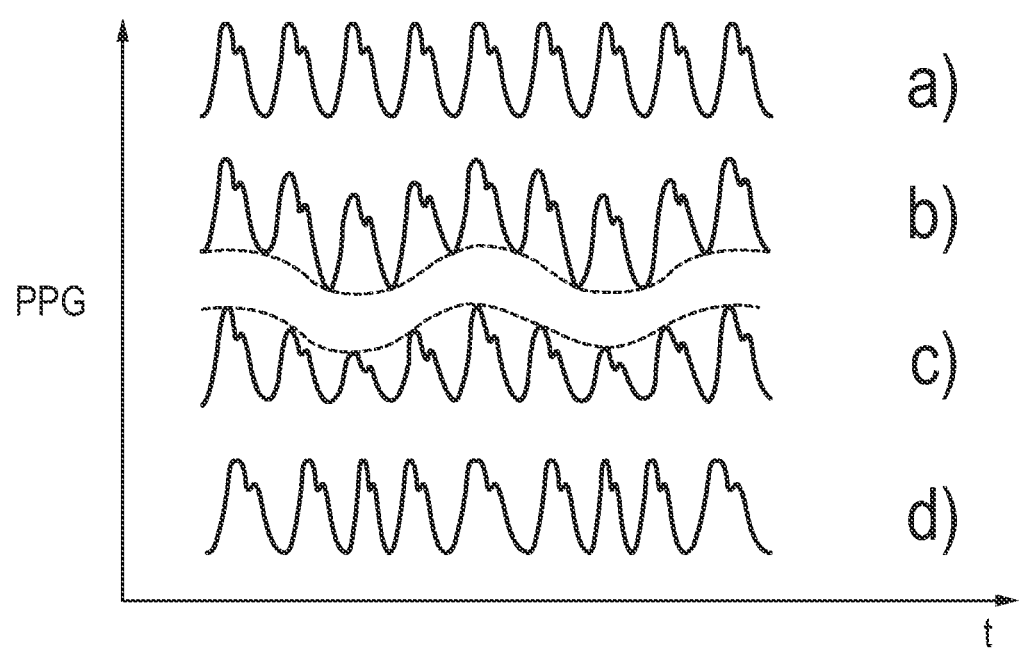
FIG. 5 shows schematic timing diagrams of different types of modulation of the plethysmography signal representing a respiration of the subject.

FIG. 5-d show different photo-plethysmography signals including the heart rate of the subject 12 and the respiration rate of the subject 12 in different modulation schemes.

FIG. 5a shows an unmodulated cardiac pulsewave form of the plethysmography signal without a superimposed respiration rate of the subject 12.

FIG. 5b shows a baseline modulation of the plethysmography signal (PPG), wherein the respiration rate is shown by the dashed baseline. Hence, the variation of the maxima or the minima of the plethysmography signal (PPG) correspond to the respiration rate of the subject 12.

FIG. 5c shows an amplitude modulated photo-plethysmography signal (PPG), wherein the heart rate is modulated by means of amplitude modulation with the respiration rate as indicated by the dashed line.

Finally, a third possible modulation is shown in FIG. 5d, wherein the pulse period of the heart rate is varied according to the respiration rate of the subject 12. In other words, the heart rate is frequency- or phase-modulated by means of the respiration signal.

In order to extract the respiration rate from the plethysmography signal (PPG) different modulation methods can be used. According to FIG. 5b-d, the respiration rate can be extracted from the photo-plethysmography signal by means of frequency filtering, amplitude demodulation or frequency demodulation.

The so-extracted respiration rate can be used to select a region of interest in the field of view of the image detection device 20 as described above.

Figure 6:
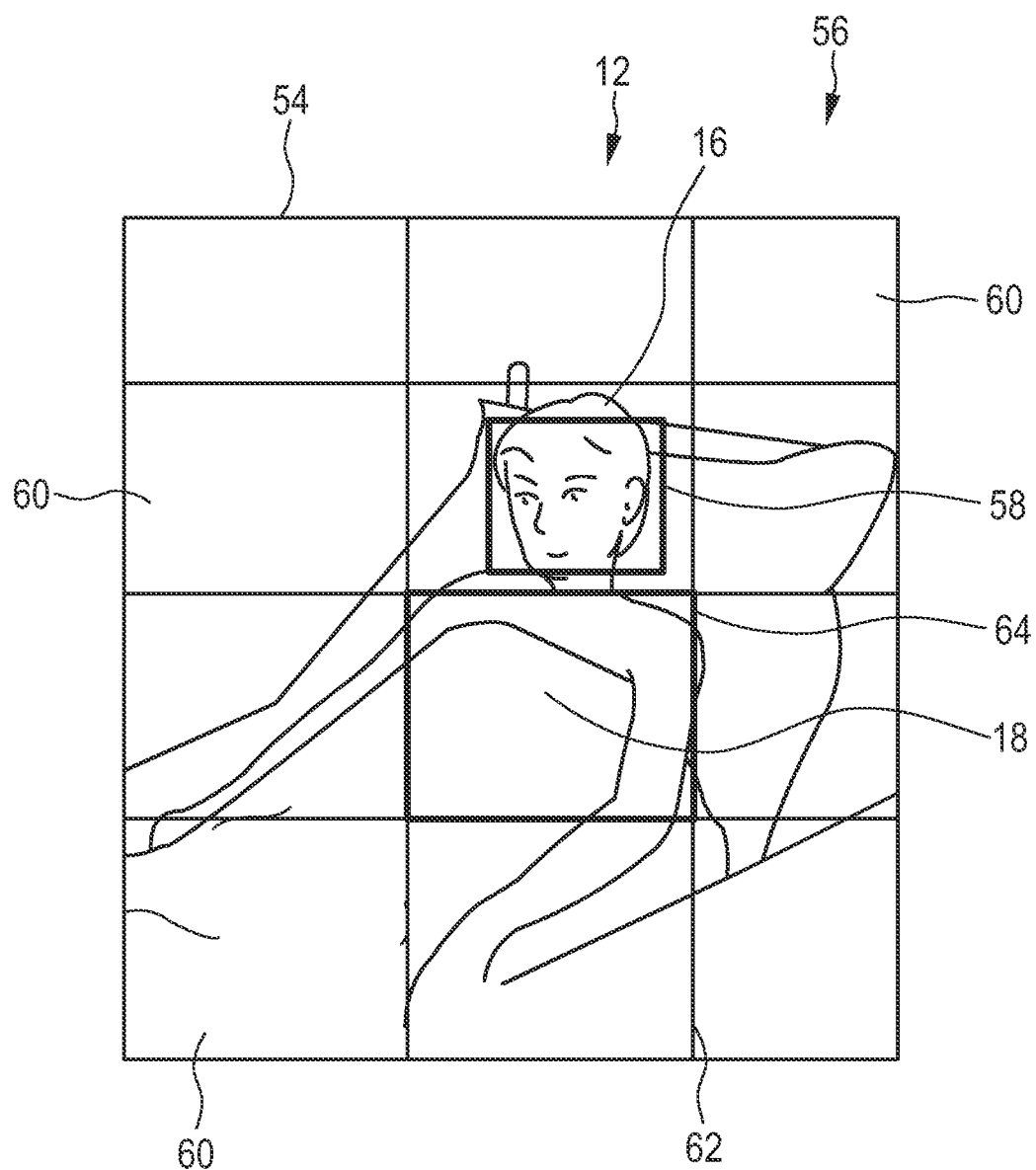
FIG. 6 shows a schematic image for illustrating the selection of a region of interest in the field of view for calculating the vital sign information.

FIG. 6 shows a schematic image for illustrating the selection of a region of interest on the basis of the respiration rate extracted from the photo-plethysmography signal (PPG).

FIG. 6 shows in general an image 54 captured by the image detection device 20 representing a field of view 56. The field of view comprises the subject 12 to be measured. First, in the field of view 56, the face of the subject 12 is determined e.g. by means of contour detection. The detection of the face of the subject 12 is indicated by an analysis region 58 shown in FIG. 6. The radiation 22 received from the analysis region 58 is evaluated by means of the determining unit 28 as described above and the plethysmography signal (PPG) is derived from color variation of the radiation 22 received from the analysis region 58.

The so-determined photo-plethysmography signal (PPG) is analyzed by means of a frequency analysis or by demodulation in particular amplitude demodulation or frequency demodulation as described above in order to extract the course respiration rate 36 from the photo-plethysmography signal (PPG). On the basis of the so-determined course respiration rate 36, a filter bandwidth is determined or a predefined filter bandwidth is selected on the basis of the course respiration rate 36.

The image 54 is in general divided in different sections 60, which is indicated by a grid 62 shown in FIG. 6. From each of the sections 60 the selection unit 38 determines the alternating signal S on the basis of motion vectors determined by means of movement pattern detection or edge detection in the respective sections 60.

The alternating signals S derived from the different sections 60 are filtered by means of the filter bandwidth determined on the basis of the course respiration rate 36 in order to determine the region of interest in the field of view 56. On the basis of the filter analysis of the alternating signals S, one of the image sections 60 is selected as region of interest 64 as indicated in FIG. 6.

In a preferred embodiment, one of the image sections 60 or a plurality of the image sections 60 comprising an alternating signal corresponding to the vital sign information from the subject 12 having a certain quality are selected as a region of interest 64 and the signals derived from the region of interest 64 may be weight by a weight factor.

After selecting the region of interest 64 as shown in FIG. 6, the vital sign information and in particular the respiration rate of the subject 12 is determined on the basis of the spatial movement of the indicative portion of the subject 12 (the chest 18), wherein the spatial movement is determined on the basis of movement pattern detection or edge detection as described above.

Hence, the region of interest 64 can be selected with high reliability and the respiration rate can be determined from the so-selected region of interest 64 and the spatial movement of the identified indicative portion of the subject 12.

Figure 7:
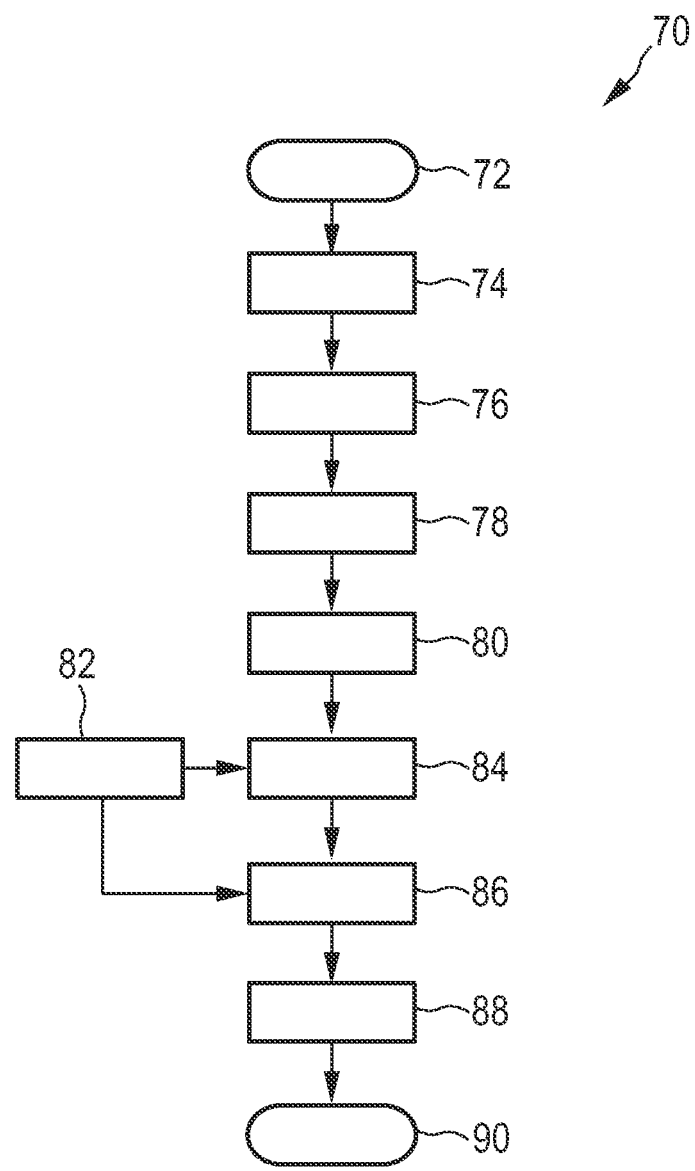
FIG. 7 shows a schematic block diagram representing the steps of an embodiment of a method for determining vital sign information from a subject.

FIG. 7 shows a schematic block diagram representing the steps of an embodiment of a method for determining vital sign information from the subject 12. The method shown in FIG. 7 is generally denoted 70. The method starts with step 72. At step 74, the face of the subject 12 is detected by means of contour detection in the image 54.

At step 76, the photo-plethysmography signal (PPG) is determined from the radiation 22 received from the face of the subject 12. At step 78, the photo-plethysmography signal (PPG) is filter analyzed by means of a filter device 34 or demodulated by means of the demodulation device 34. On the basis of the filter process and/or the demodulation the course respiration rate 36 is determined. On the basis of the course respiration rate 36 a filter bandwidth is selected or determined as shown by step 80. At step 82, movement patterns are determined in the sections 60 of the image 54 and the alternating signals S are determined for each of the image sections 60. At step 84, the different alternating signals S of the different image sections 60 are filtered by means of the filter bandwidth on the basis of the filtered alternating signals, the region of interest 64 is selected at 86.

At step 88, the breathing rate is calculated from the movement pattern determined from the region of interest 64 which is determined in step 82 or separately determined. The breathing rate calculation is described in the following.

The method 70 ends at step 90.

Figure 8:
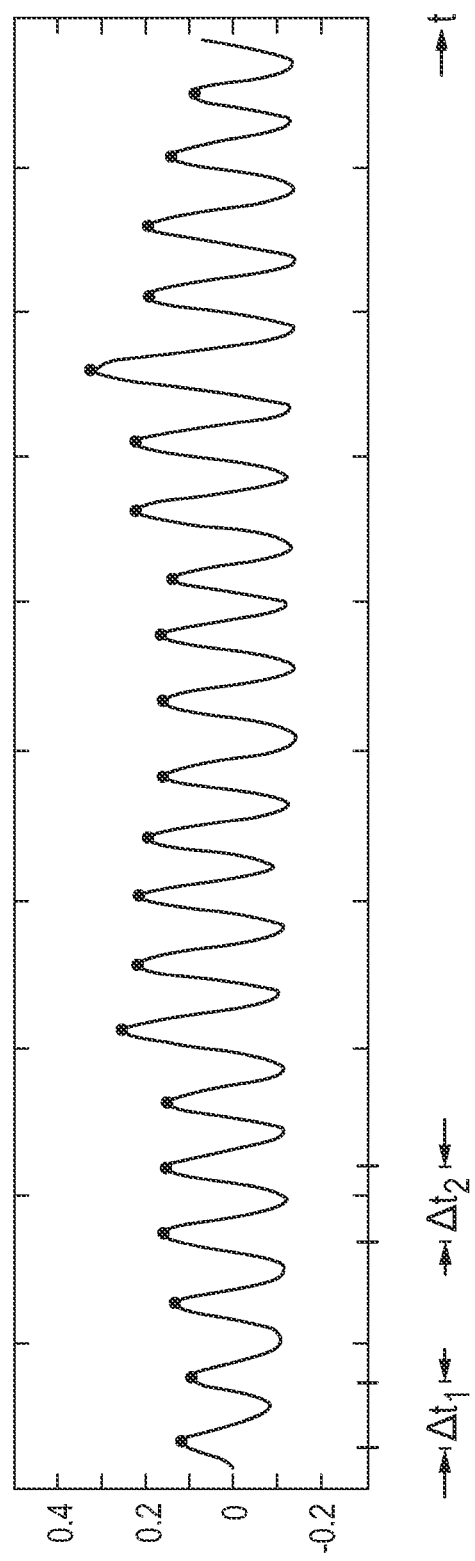
FIG. 8 shows a schematic timing diagram of the vital signal derived from the region of interest of the field of view.

FIG. 8 shows a timing diagram of a vital sign information derived from the alternating signals of the region of interest 64 and is generally denoted by R(t). The vital sign information R corresponds to the respiration signal derived from the motion of the chest 18 of the subject 12. From the so-determined respiration signal R, the respiration rate can be determined on the basis of the maxima of the respiration signal R as indicated by dots in FIG. 7. The time distances between the dots are shown in FIG. 8 as an example by $\Delta t1$ and $\Delta t2$. The respiration rate is calculated by means of the reciprocal value of the time distances $\Delta t1$, $\Delta t2$ between the maxima of the respiration signal R or an average of the time distances shown in FIG. 8.

Hence, the respiration rate can be easily derived from the movement of the chest 18 and since the region of interest 64 is automatically determined on the basis of the plethysmography signal (PPG), the respiration rate can be determined from the image 54 with high reliability and high preciseness.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or an does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

Furthermore, the different embodiments can take the form of a computer program product accessible from a computer usable or computer readable medium providing program code for use by or in connection with a computer or any device or system that executes instructions. For the purposes of this disclosure, a computer usable or computer readable medium can generally be any tangible device or apparatus that can contain, store, communicate, propagate, or transport the program for use by or in connection with the instruction execution device.

In so far as embodiments of the disclosure have been described as being implemented, at least in part, by software-controlled data processing devices, it will be appreciated that the non-transitory machine-readable medium carrying such software, such as an optical disk, a magnetic disk, semiconductor memory or the like, is also considered to represent an embodiment of the present disclosure.

The computer usable or computer readable medium can be, for example, without limitation, an electronic, magnetic, optical, electromagnetic, infrared, or semiconductor system, or a propagation medium. Non-limiting examples of a computer readable medium include a semiconductor or solid state memory, magnetic tape, a removable computer diskette, a random access memory (RAM), a read-only memory (ROM), a rigid magnetic disk, and an optical disk. Optical disks may include compact disk-read only memory (CD-ROM), compact disk-read/write (CD-R/W), and DVD.

Further, a computer usable or computer readable medium may contain or store a computer readable or usable program code such that when the computer readable or usable program code is executed on a computer, the execution of this computer readable or usable program code causes the computer to transmit another computer readable or usable program code over a communications link. This communications link may use a medium that is, for example, without limitation, physical or wireless.

A data processing system or device suitable for storing and/or executing computer readable or computer usable program code will include one or more processors coupled directly or indirectly to memory elements through a communications fabric, such as a system bus. The memory elements may include local memory employed during actual execution of the program code, bulk storage, and cache memories, which provide temporary storage of at least some computer readable or computer usable program code to reduce the number of times code may be retrieved from bulk storage during execution of the code.

Input/output, or I/O devices, can be coupled to the system either directly or through intervening I/O controllers. These devices may include, for example, without limitation, keyboards, touch screen displays, and pointing devices. Different communications adapters may also be coupled to the system to enable the data processing system to become coupled to other data processing systems, remote printers, or storage devices through intervening private or public networks. Non-limiting examples are modems and network adapters and are just a few of the currently available types of communications adapters.

The description of the different illustrative embodiments has been presented for purposes of illustration and description and is not intended to be exhaustive or limited to the embodiments in the form disclosed. Many modifications and variations will be apparent to those of ordinary skill in the art. Further, different illustrative embodiments may provide different advantages as compared to other illustrative embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated. Other variations to the disclosed embodiments can be understood and effected by those skilled in the art in practicing the claimed invention, from a study of the drawings, the disclosure, and the appended claims.

The invention claimed is:

1. An apparatus for determining vital sign information from a subject, comprising:
   a detection unit that detects radiation received from the subject in a field of view,
   a first determining unit that determines a first time dependent signal from the radiation received from the subject,
   an evaluation unit that derives at least one parameter from the first time dependent signal,
   a selection unit that selects an area in the field of view on the basis of the detected radiation and the at least one parameter,
   a second determining unit that determines a second time dependent signal from the radiation received from the selected area, and
   an analysis unit that analyses the second time dependent signal and determines the vital sign information on the basis of the analysis of the second time dependent signal.

2. The apparatus as claimed in claim 1, wherein the evaluation unit comprises a frequency determining device that determines a frequency from the first time dependent signal as the at least one parameter.

3. The apparatus as claimed in claim 1, wherein the evaluation unit comprises a demodulation unit that determines a frequency from the first time dependent signal as the at least one parameter.

4. The apparatus as claimed in claim 3, wherein the demodulation unit is a frequency demodulation unit that demodulates the first time dependent signal as a frequency modulated signal.

5. The apparatus as claimed in claim 3, wherein the demodulation unit is an amplitude demodulation unit that demodulates the first time dependent signal as an amplitude modulated signal.

6. The apparatus as claimed in claim 1, wherein the evaluation unit comprises a filter device that filters the first time dependent signal and that determines the at least one parameter.

7. The apparatus as claimed in claim 1, wherein the detection unit comprises an imaging device that determines image data from the field of view.

8. The apparatus as claimed in claim 1, wherein the first time dependent signal is based upon a wavelength variation of the radiation received from the subject.

9. The apparatus as claimed in claim 7, wherein the selection unit is adapted to determine a plurality of alternating signals from different areas of the field of view and wherein the selection unit is adapted to select the area for determining the second time dependent signal on the basis of the alternating signals (S) and on the basis of the at least one parameter.

10. The apparatus as claimed in claim 9, wherein the alternating signals determined from the different areas of the field of view correspond to movement pattern in the field of view and are determined on the basis of pattern detection.

11. The apparatus as claimed in claim 9, wherein the at least one parameter is a bandwidth that filters the alternating signals.

12. The apparatus as claimed in claim 1, wherein the first time dependent signal is received from a skin of the subject.

13. The apparatus as claimed in claim 1, wherein the detection unit comprises a first camera that determines the first time dependent signal and a second camera that determines the second time dependent signal.

14. The apparatus as claimed in claim 1, wherein the first time dependent signal is a plethysmography signal.

15. A method for determining vital sign information from a subject, comprising:

detecting radiation received from the subject in a field of view, determining a first time dependent signal from the radiation received from the subject, deriving at least one parameter from the first time dependent signal, selecting an area in the field of view on the basis of the detected radiation and the at least one parameter, determining a second time dependent signal from the radiation received from the selected area, and analyzing the second time dependent signal and determining the vital sign information from the analyzed second time dependent signal.

16. The method as claimed in claim 15, wherein the first time dependent signal is based upon a wavelength variation of the radiation received from the subject; and the method further includes:

determining a plurality of alternating signals from different areas of the field of view and wherein the selection unit is adapted to select the area for determining the second time dependent signal on the basis of the alternating signals (S) and on the basis of the at least one parameter.

17. The apparatus as claimed in claim 1, wherein the a first determining unit, the evaluation unit, the selection unit, the second determining unit, and the analysis unit comprise a computer.

* * * * *